(12) United States Patent
Gu et al.

(10) Patent No.: US 11,117,919 B2
(45) Date of Patent: Sep. 14, 2021

(54) ICARISIDE COMPOUND, PREPARATION METHOD THEREOF, AND APPLICATION THEREOF

(71) Applicant: FOSHAN GOLDEN HEALTH TECHNOLOGY CO., LTD., Guangdong (CN)

(72) Inventors: Lianquan Gu, Guangdong (CN); Changyou Wu, Guangdong (CN); Jinlin Zhou, Guangdong (CN); Yujing Lu, Guangdong (CN); Tianmiao Ou, Guangdong (CN); Baohua Huang, Guangdong (CN); Liwei Lin, Guangdong (CN)

(73) Assignee: GOLDEN HEALTH (GUANGDONG) BIOTECHNOLOGY CO. LTD., Guangdong (CN)

( * ) Notice: Subject to any disclaimer, the term of this patent is extended or adjusted under 35 U.S.C. 154(b) by 42 days.

(21) Appl. No.: 16/444,367

(22) Filed: Jun. 18, 2019

(65) Prior Publication Data
US 2019/0300560 A1  Oct. 3, 2019

Related U.S. Application Data

(62) Division of application No. 15/745,784, filed as application No. PCT/CN2015/082591 on Jun. 29, 2015, now abandoned.

(30) Foreign Application Priority Data

May 20, 2015 (CN) .......................... 201510264195.5

(51) Int. Cl.
| | | |
|---|---|---|
| C07H 17/07 | (2006.01) |
| A61P 37/04 | (2006.01) |
| A61P 31/12 | (2006.01) |
| A61P 31/06 | (2006.01) |
| A61P 35/00 | (2006.01) |
| A61K 8/60 | (2006.01) |
| A61K 9/00 | (2006.01) |
| C07H 1/08 | (2006.01) |
| C12P 19/60 | (2006.01) |
| C07H 1/00 | (2006.01) |
| A61Q 19/00 | (2006.01) |
| G01N 33/50 | (2006.01) |

(52) U.S. Cl.
CPC ............. *C07H 17/07* (2013.01); *A61K 8/602* (2013.01); *A61K 9/0014* (2013.01); *A61P 31/06* (2018.01); *A61P 31/12* (2018.01); *A61P 35/00* (2018.01); *A61P 37/04* (2018.01); *A61Q 19/00* (2013.01); *C07H 1/00* (2013.01); *C07H 1/08* (2013.01); *C12P 19/60* (2013.01); *G01N 33/5055* (2013.01)

(58) Field of Classification Search
CPC ......... A61P 37/04; A61P 31/12; A61P 31/06; A61P 35/00; C07H 17/07; C07H 1/08; C07H 1/00; A61K 8/602; A61K 9/0014; A61K 8/498; A61K 8/60; A61K 9/0019; A61K 31/7048; A61Q 19/00; C12P 19/60
See application file for complete search history.

(56) References Cited

U.S. PATENT DOCUMENTS

2009/0170787 A1* 7/2009 Park .................. A61K 8/498
514/27

FOREIGN PATENT DOCUMENTS

CN          1969952 A  *  5/2007

* cited by examiner

*Primary Examiner* — Sahar Javanmard
(74) *Attorney, Agent, or Firm* — Michael J. Feigin, Esq.; Feigin and Fridman LLC (57) ABSTRACT

An icariside compound as shown in Formula I wherein the compound is a natural chemical component in the traditional Chinese herbal epimedium or a chemically modified or a totally synthetic product based on the natural component. The compound can be used for preparing pharmaceuticals, health care products, cosmetic and skin care products and the like for improvement of immunity in a human body.

3 Claims, 5 Drawing Sheets

FIG.1 reaction of enzymatic coversion of icariin to icariside I

FIG.2 reaction of enzymatic conversion of epimedoside A to icariside C

FIG.3 reaction of chemical and enzymatic conversion of icariin to icariside compound (Y-5XS-1)

FIG.4 reaction of chemical conversion of icariside I to icariside compound (Y-3XS-1)

FIG.5 production of IFN-γ promoted and stimulated by the pharmaceutical icariside I (PBMCs treated with anti-CD3) and promotion rate.

FIG.6 production of IFN-γ promoted and stimulated by the pharmaceutical icariside I (PBMCs treated with anti-CD3 and anti-CD28) and promotion rate.

FIG.7 the pharmaceutical icariside I promotes production of IFN-γ by mixed lymphocytes culture FIG.8 effects of different icariside I componds on levels of IFN-γ produced by mixed lymphocytes
[icariside I compounds: (1) icariin; (2)icariside I; (3) icariside C; (4) Y-3XS-1; (5) Y-5XS-1; (6) Y-4'XS-1]

FIG.9 effect of pharmaceutical icariside I on level of IFN-γ produced by PBMCs and PFMCs FIG.10 effect of icariside I on xenograft tumor of nude mice (growth curve)

FIG. 11 effect of icariside I on xenograft tumor in nude mice (final change of tumor weight)

ICARISIDE COMPOUND, PREPARATION METHOD THEREOF, AND APPLICATION THEREOF

CROSS REFERENCE TO RELATED APPLICATIONS

This application is a divisional application of U.S. patent application Ser. No. 15/745,784, filed Jan. 18, 2018, which is the United States National Stage entry under 35 U.S.C. 371 of PCT/CN2015/082591 filed on Jun. 29, 2015, which in turn claims the priority of Chinese patent application No. 201510264195.5 "ICARISIDE COMPOUND, PREPARATION METHOD THEREOF, AND APPLICATION THEREOF" filed on May 20, 2015. These applications are each incorporated by references herein in their entireties.

BACKGROUND

Human immunity refers to the ability of the body to protect against causative factors outside or within host cells from infection or invasion, i.e. the ability of the body to maintain a normal and stable environment within the body. In the environments where people live, air, water, food, and most items we contact in daily life, for example, contains a variety of harmful microorganisms such as bacteria, viruses, *Mycoplasma, Chlamydia*, fungi and other pathogens (causative factors outside a host cell). Human body may also be affected by the environmental changes, the emergence of a latent virus or bacteria in the host cell, or infection or invasion of cancer cells produced by gene mutation and the like (causative factors within a host cell). When the body is invaded or infected by these causative factors, the body normally will produce corresponding antibodies or various cytokines (such as interferon, etc.) through its own immune system to protect against the infection or invasion of pathogens by phagocytosis and eradication. When the immunity (antibodies or cytokines etc.) produced by human immune system is not sufficient to fight against the disease causative factors, people get sick.

In order to maintain good health, to prevent or reduce the incidence of diseases, it is of great importance to improve human immunity. Using pharmaceuticals to enhance immunity is an effective method for prevention and treatment of infective diseases, cancers and so on, which is called immunotherapy. Effective pharmaceuticals discovered and developed for improving human immunity is important for people with weak immunity, especially those suffering from autoimmune diseases.

In general, only few pharmaceuticals can be used in immunotherapy. Currently, the clinical applicable pharmaceuticals for human immunity enhancement mainly include macromolecular peptides or protein pharmaceuticals such as thymosin, immunoglobulin, interferon and the like. However, these are specific for certain diseases which greatly limit their applications. In addition, they are easy to be degraded which have a short half-life and poor bioavailability and which are difficult to be large-scale synthesized, separated and purified.

Formulations developed to improve human immunity based on natural products are basically health care products whose actual effects cannot be guaranteed. So far, attempts to find small molecular compounds with good effects on enhancing immunity are not yet successful. No small molecular compound for immunotherapy has been reported.

Epimedium is a traditional Chinese herbal medicine. Currently, its utility is usually under the guidance of TCM theory with epimedium plant boiled for decoction, soaked in wine, prepared into ointment, or prepared into pellets or pills, etc. However, systematic studies on the separation of active components therein are rare, in particular that on icariside I and icariside C due to their extremely low content (while its homologue, icariin, has higher content) leading to difficulty in conducting an effective research, let alone industrial application.

FIELD OF THE DISCLOSURE

The present invention relates to icariside compounds, preparation methods and potential applications thereof. These compounds promote human cells to produce IFN-γ, which significantly improves human immunity and can be applied in treatment of diseases, health care products, cosmetic and skin care products, and the like.

SUMMARY

The present inventors have long been researching the active components in traditional Chinese herbal medicine and their applications in immunotherapy. The present inventors have established an immunological test model based on determination of the level of IFN-γ produced in human peripheral blood mononuclear cells (PBMCs). By this model, compounds having promotion (or inhibition) effects on human peripheral blood mononuclear cells (PBMCs) to produce γ-interferon can be screened out from chemical components from various sources including traditional Chinese herbal medicine, medicinal plants and so on. Since the γ-Interferon is an important protein (cytokine) in human body's immune system to resist attacks from diseases, its production level in body directly relates to the body's immunity. Therefore, the model is an ideal tool to screen and find functional pharmaceuticals for improving human immunity.

During the process of screening, the present inventors surprisingly found that, the two compounds, icariside I and icariside C, which are present in epimedium at very low contents showed significant effect in promoting PBMCs to generate IFN-γ while other natural chemical compounds contained in epimedium have nearly no relative activities. Results of the research showed that icariside I and icariside C can directly promote human cells to generate the important immune protein IFN-γ, indicating that such compounds have important promising applications in improving human immunity.

The present inventors used natural compounds for example icariin, epimedoside A, icariside I or icariside C as basic raw material to produce other icariside compounds through chemical conversion (semi-synthesis). Some icariside compounds can also be obtained totally by synthesis. By screening test with the model, it is proved that these substances also have an activity similar to that of icariside I or icariside C.

Therefore, a first object of the present invention is to provide an icariside compound (as shown in formula I).

Formula I

Groups represented by $R_1$, $R_2$, and $R_3$ in Formula I are defined as follows:

(1) $R_1$ is any of H, OH, $OCH_3$, $CH_3COO$, $CH_3$, $CF_3$, $NH_2$, $CH_3NH$, $CH_3CONH$, CN, Br, Cl, F, etc.;

(2) $R_2$ is any of H, OH, $OCH_3$, $CH_3COO$, $NH_2$, $CH_3NH$, $(CH_3)_2N$, $CH_3CONH$, CN, etc.;

(3) $R_3$ is selected from H, OH, $OCH_3$, $CH_3COO$, $CH_3$, $CF_3$, and, $C_1$-$C_6$—$NH_2$ (wherein the $C_1$-$C_6$ is an alkyl group, a cycloalkyl group, an olefin group, a cyclic olefin group, in particular a cyclopentyl group, a cyclohexylamino group; and a morpholinyl group or a methylpiperazinyl group having 1-6 carbon atoms), $NH_2$, $CH_3NH$, $(CH_3)_2N$, $(CH_3CH_2)_2N$, $CH_3CONH$, CN, Br, Cl, F, amino acid acyl, amino acid acylamino(R'—CH—CONH—), oligopeptideacyl, oligopeptide amido group, etc.

The present invention obtains icariside I (i.e. $R_1$=OH, $R_2$=OH, and $R_3$=$OCH_3$) and icariside C (i.e. $R_1$=OH, $R_2$=OH, and $R_3$=OH) through separation and purification from epimedium extract [icariside I and icariside C have a low content in traditional Chinese medicine epimedium, while homologues thereof—icariin (with $R_1$=OH, $R_2$=rhamnoside Rha, $R_3$=$OCH_3$ in Formula I) and epimedoside A (with $R_1$=OH, $R_2$=rhamnoside Rha, $R_3$=OH in Formula I) have relatively higher contents].

Thus, a second object of the present invention is to transform the abundant epimedium icariin into icariside I using for example enzymatic conversion technology and to transform the icariside A into icariside C.

A further object of the present invention is to provide a method of obtaining icariside compounds as shown in Formula I by derivatization of natural products for example icariin, epimedoside A, icariside I and icariside C.

The γ-interferon in human body is an important anti-disease immune protein (cytokine) which can inhibit the replication of virus and can also effectively counteract against other pathogenic substances such as invasion of bacteria, cancer cells, etc. and infection. We further tested the icariside compounds (alone or in combination with antigen(s)) with a test of promotion of generation of anti-tuberculosis infection cytokines, a test of inhibition of tumor growth in mice and xenograft tumor trials in nude mice. Results proved that icariside compounds can significantly improve the body's immunity and effectively improve the ability of the body to protect against infection or invasion of causative factors (outside or within host cells). These compounds can be used for prevention and treatment of infective diseases for example influenza, hepatitis B, hepatitis C, and tuberculosis, and tumor progression and metastasis, etc. These compounds show potential in development of a new pharmaceutical for cellular immune therapy. They can also be used for preparation of various products related to human immune system improvement such as health care medicines, beverages, cosmetic and skin care products.

Thus, a further object of the present invention is to provide a class of icariside compounds of Formula I, pharmaceuticals, health products, food and cosmetic and skin care products comprising icariside I, icariside C and the like as main ingredient for prevention and treatment of human immunity-related diseases. These products may comprise one, two or more icriside compound(s) as main effective ingredient(s) for example icariside I or icariside C, or both, and acceptable adjuvant(s) in pharmaceutical, health products, food, or cosmetic or skin care products and the like. The products can be prepared in different forms of formulations for example tablets, pills, capsules, injection solutions, suspensions, emulsions, liniments for external use, and mask.

The present invention proves by toxicology research that icariside I and icariside C have low toxicity and side effects ($DC_{50}$>2 g/kg body weight) which is safe for use.

In addition, all the results and achievements of the present invention are based on the very effective screening model established by the present inventors. Therefore, a further objective of the present invention is to provide an experimental model for screening substances having impacts (either enhance or inhibit) on immunity. Small molecular compounds having the effect of improving or inhibiting human immunity were screened out by the model by applying exogenous antigens to stimulate human peripheral blood mononuclear cells (PBMCs) to produce cytokine IFN-γ, adding the pharmaceuticals to be tested to the mixed system of exogenous antigens and PBMCs, and measuring the effect on production level of IFN-γ. Specifically, the method prepared human peripheral blood mononuclear cells (PBMCs) by isolation from fresh blood collected from healthy people. Then the exogenous antigens for example monoclonal stimulatory molecules Anti-CD3, Anti-CD3/Anti-CD28, PBMCs from different people, or human cells infectively stimulated by other causative factors (e.g. viruses, bacteria and cancer cells) were applied for stimulation. The peripheral blood mononuclear cells, after the above stimulation, produced new cytokine IFN-γ. Then the pharmaceuticals to be tested (compounds to be screened) were added at different concentrations in a gradient and well-mixed. The PBMCs after completion of stimulation were seeded and cultured in a 96-well mini round bottom plates and were incubated in 5% $CO_2$ at 37° C. in an incubator. Finally, by using ELISA techniques, the levels of IFN-γ produced in the culture were measured at different incubation time. Increased level of produced IFN-γ indicates that the tested compound has the effect of improving the immunity. On the other hand, decreased level of produced IFN-γ indicates that the tested compound has the effect of inhibiting human immunity. Thus, the present method can also be used to screen small molecular compounds having an effect of inhibiting human immunity, i.e. immune inhibitor.

DETAILED DESCRIPTION

The following examples further illustrate the embodiments of the present invention.

Example 1

Preparation of Icariside I (1) Preparation of Icariside I by Separation from Epimedium.

According to the method reported by Li Wenkui, et al. (Herbal, 1995, 26 (9), 453-455), icariside I was separated and purified with a content of more than 95% from the whole plant of epimedium. The chemical structure of the product was characterized by 1H NMR, Mass spectroscopy, and other instrumentations.

(2) Preparation of Icariside I by Enzymatic Conversion of Icariin as Raw Material.

A. Preparation of icariin: According to the method reported by Li Wenkui, et al. (Herbal, 1995, 26 (9), 453-455), icariin was separated and purified with a content of more than 95% from the whole plant of epimedium. The chemical structure of the product was characterized by $^1$H NMR, Mass spectroscopy, and other instrumentations.

Figure 1:
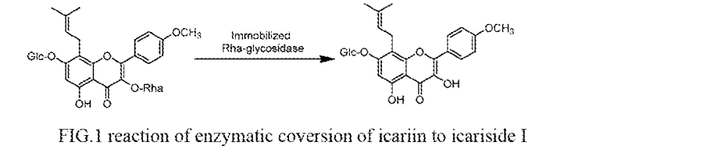
FIG. 1 shows the reaction of enzymatic conversion of icariin to icariside I in Example 1.

B. Preparation of icariside I: 2 g of icariin (purity 98%) was dissolved in a pH6.8 phosphate buffer, and then 1 g of immobilized rhamnosidase was added. The mixture was stirred at 60° C. for 24 hours for reaction. The mixture was filtered to collect solids after crystallization. Then the solid were recrystallized with methanol to obtain 1.3 g icariside I (purity 95%). The chemical structure of the product was characterized by $^1$H NMR, Mass spectroscopy, and other instrumentations. The specific reaction formula was shown in FIG. 1.

Example 2

Preparation of Icariside C (1) Preparation of Icariside C by Separation from Epimedium.

According to the method reported by Li Wenkui, et al. (Herbal, 1995, 26 (9), 453-455), icariside C with a content of more than 95% was obtained after separation and purification from the whole plant of epimedium. The chemical structure of the product was characterized by $^1$H NMR, Mass spectroscopy, and other instrumentations.

(2) Preparation of Icariside I from Epimedoside a as Raw Material by Enzymatic Conversion.

A. Preparation of epimedoside A: epimedoside A is one of the components with a higher content in epimedium. According to the method reported by Xu Sui Xu et al. (Herbs, 1981, 14, 24-26), epimedoside A with a content of more than 95% was obtained by separation and purification from the whole plant of epimedium. The chemical structure of the product was characterized by $^1$H NMR, Mass spectroscopy, and other instrumentations.

Figure 2:
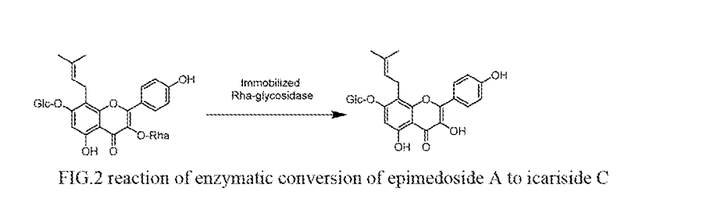
FIG. 2 shows the reaction of enzymatic conversion of epimedoside A to icariside C in Example 2.

B. Preparation of icariside C: Icariside C was obtained by removal of 3-O-rhamnosyl group from epimedoside A with rhamnosidase by the method in Examples 1 (2) using epimedoside A as raw material. The chemical structure of the product was characterized by $^1$H NMR, Mass spectroscopy, and other instrumentations. The specific reaction formula was shown in FIG. 2.

Example 3

Preparation of Icariside Compounds Based on Modification of the $R_1$ Group

Using icariin as raw material, the OH group of $R_1$ was selectively transformed into another group by a chemical method (the process does not affect glycosyl groups present in the molecule). Then, by applying the method in Example 1 (2), the $R_2$ Rha group of the modified icariin was removed with an enzymatic method to obtain the desired icariside compounds.

Figure 3:
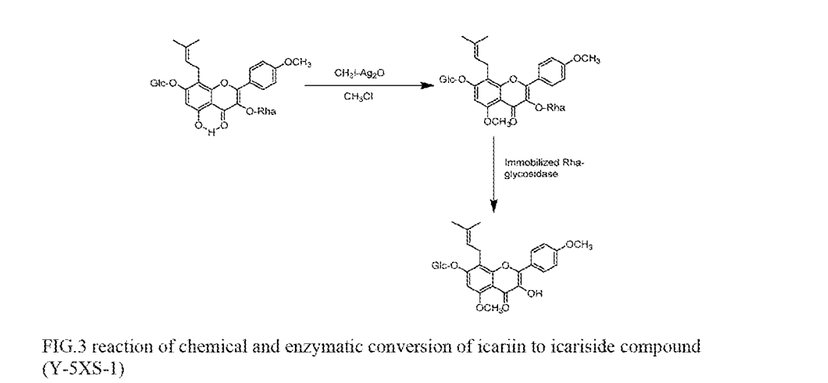
FIG. 3 shows chemical and enzymatic conversion of icariin to icariside compound (Y-5XS-1) in Example 3.

Preparation Example: 2 ml chloroform was added to 50 mg icariin followed by addition of 10 mg iodomethane ($CH_3I$) and addition of 10 mg silver oxide ($Ag_2O$). Then, the solution was stirred at room temperature for 24 hours. After reaction, chloroform was removed by rotary evaporation. The residue was re-dissolved with 95% ethanol and was purified by column chromatography (silica gel column) to obtain the product with $R_1$ being a methoxy group. Finally, by applying the method in Example 1 (2), the $R_2$ Rha group in the modified icariin was removed with an enzymatic method. The desired icariside compound (Y-5XS-1) with $R_1$ being a methoxy group was obtained and the chemical structure of the product was characterized by $^1$H NMR, Mass spectroscopy, and other instrumentations. The specific reaction formula was shown in FIG. 3.

Example 4

Preparation of Icariside Compounds Based on Modification of the $R_2$ Group

Using icariside I as raw material, the OH group at position 3 of icariside I (i.e. $R_2$=OH) was selectively modified to obtain the desired icariside compound.

Figure 4:
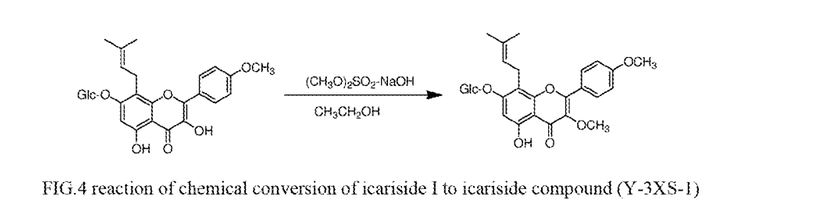
FIG. 4 shows chemical conversion of icariside I to another icariside compound (Y-3XS-1) in Example 4.

Preparation Example: 5 ml of ethanol (95%), and 30 mg dimethyl sulfate were added to 100 mg of icariside I, and then 15 mg sodium hydroxide was added. The mixture was stirred at room temperature for 5 hours. After completion of the reaction, 20 ml of water was added to the mixture and then extraction with ether was performed. The separated ether layer was dried with anhydrous sodium sulfate. After removal of ether, the crude product was dissolved in 95% ethanol and then purified by column chromatography (silica gel column) to obtain the desired icariside compound (Y-3XS-1) with $R_2$ being a methoxy group. The chemical structure of the product was characterized by $^1$H NMR, Mass spectroscopy, and other instrumentations. A small amount of icariside compound (Y-3XS-1) with $R_1$ being a methoxy group can also be obtained by this method. The specific reaction formula is shown in FIG. 4.

Example 5

Preparation of Icariside Compounds Based on Modification of the $R_3$ Group

Using epimedoside A as starting material, the OH group of $R_3$ was selectively transformed into another group by a chemical method (the process does not affect glycosyl groups present in the molecule). Finally, by applying the method in Example 1 (2), the $R_2$ Rha group in the modified icariin product was removed with an enzymatic method. The desired icariside compounds were obtained.

Preparation Example: 5 ml of isopropanol containing 5% water and 30 mg diisopropyl sulfate were added to 100 mg epimedoside A followed by addition of 15 mg sodium hydroxide. The mixture was stirred at room temperature for 10 hours. After completion of the reaction, 20 ml of water was added and then extraction with ether was performed. The ether layer was dried with anhydrous sodium sulfate. After removal of ether, the crude product was dissolved in ethanol and then purified by column chromatography (silica gel column) to obtain the modified product with $R_3$ being an isopropoxy group. Finally, by applying the method in Example 1 (2), the $R_2$ Rha group in the modified icariin product was removed with an enzymatic method. The desired icariside compound (Y-4' XS-1) with $R_3$ being an isopropoxy group was obtained and the chemical structure of the product was characterized by $^1$H NMR, Mass spectroscopy, and other instrumentations.

Example 6

Test of Using Icariside I to Promote Human γ-Interferon Production and to Improve Human Immunity (I)

Effect of icariside I on promoting normal human peripheral blood mononuclear cells (PBMCs subjected to mAb treatment) to produce γ-interferon (interferon-gamma, IFN-γ) (an experimental model mimicking enhancing immunity in human body).

(1) Preparation of icariside I solution for the test. 10 mg icariside I was dissolved in 1 ml DMSO (with initial concentration of 10 mg/ml). The solution was then transferred into small vials and stored in a freezer at −80° C. for future use.

(2) Preparation of normal human peripheral blood mononuclear cells (PBMCs).

The whole blood samples were drawn from peripheral vein of healthy volunteers. Heparin (blood:heparin=10 ml: 80 μl) was used for anticoagulation. Then, it is diluted with equal volume of Hank's solution. The diluted blood samples were slowly laid on the Ficoll separation solution (Ficoll to diluted blood ratio is 3:4) followed by Ficoll density gradient centrifugation (22° C. 2200 r/min, 20 min). After centrifugation, samples were divided into three layers in the tube. At the interface between the top and middle layers, there was a narrow band which is a mononuclear cell-based yellow-white cloud layer. The peripheral blood mononuclear cells (PBMCs) were drawn and transferred into another centrifuge tube with a pipette. The obtained PBMCs were washed with Hank's solution twice (1800 r/min, 8 min). The supernatant was removed after the last centrifugation and the residue was added with RPMI 1640 complete medium to re-suspend the cells followed by mixing. The mononuclear cells were counted with trypan blue solution. Desired concentration was obtained by adjusting cell number by adding RPMI 1640 complete medium.

(3) in vitro culture of lymphocytes with stimulation by a pharmaceutical

The cell concentrations of freshly isolated peripheral blood mononuclear cells (PBMCs) were adjusted to $2 \times 10^6$/ml with RPMI 1640 complete medium. Then a stimulatory molecule monoclonal Anti-CD3 (1 μg/ml) or Anti-CD3 (1 μg/ml)/Anti-CD28 (1 μg/ml) was added or not added, and three different concentrations (at a gradient) of the pharmaceutical icariside I (at a final concentration of 1 ng/ml, 10 ng/ml, 100 ng/ml) were added and then well-mixed. The cells after stimulation with the pharmaceutical were seeded and cultured in 96-well round-bottom plates. The cell concentration per well was $4 \times 10^5$/ml (200 μl/well) with each of the stimulation conditions repeated for three wells. The cells were incubated at 37° C. with 5% $CO_2$ in an incubator for four different time periods: 12 h, 24 h, 36 h and 48 h. Finally, the supernatant of each well with different culture time was taken respectively for test and measurement.

(4) ELISA Analysis of Production of Cytokine IFN-γ

Figure 5:
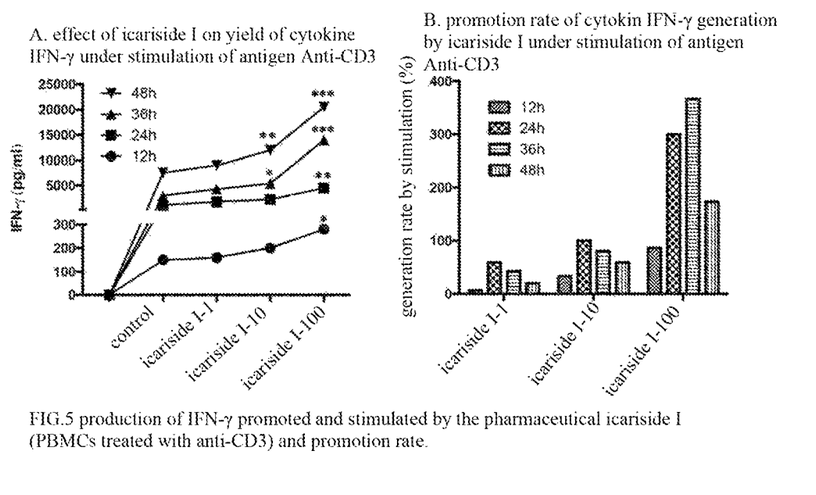
FIG. 5 shows the pharmaceutical icariside I (PBMCs subjected to anti-CD3 treatment) stimulating and promoting the generation of IFN-γ with promotion percentage in Example 6.
Figure 6:
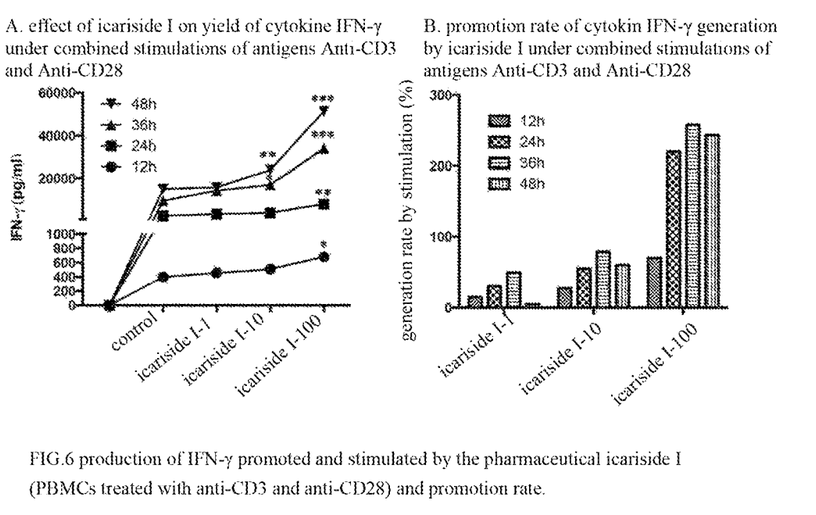
FIG. 6 shows the pharmaceutical icariside I (subjected to the combined treatment of anti-CD3 and anti-CD28) stimulating and promoting the generation of IFN-γ with promotion percentage in Example 6.

The collected cell culture supernatants with different culture time were detected with ELISA to measure the amount of cytokine IFN-γ produced. The reagents, antibodies, and testing methods used for ELISA were based on the operational instructions for use provided by the manufacturer. All data analysis and graph were made using the software GraphPad Prism 5 version. The results were shown in FIGS. 5 and 6. FIGS. 5 and 6 showed that icariside I significantly enhanced the IFN-γ level produced by PBMCs induced by a monoclonal stimulatory molecule and the enhancement was dose-dependent with icariside I.

Different concentrations (ng/ml) of the pharmaceutical icariside I were added to PBMCs treated with anti-CD3. FIG. 5A: icariside I significantly increased the production of the cytokine IFN-γ in a time and dose dependent way. FIG. 5B: percentage of IFN-γ production promoted by icariside I at different concentrations and at different time points.

Different concentrations (ng/ml) of the pharmaceutical icariside I were added to PBMCs treated with anti-CD3 and anti-CD28. FIG. 6A: curve of change of the amount of produced cytokine IFN-γ with the pharmaceutical icariside I at different concentrations and at different time points. FIG. 6B: promotion rate by the pharmaceutical icariside I at different concentrations and at different time points. *P<0.05; -*P<0.01.

Example 7

Test of Using Icariside I to Promote Human γ-Interferon Production and to Improve Human Immunity (II)

Effect of icariside I on promotion of γ-interferon (interferon-gamma, IFN-γ) production by human peripheral blood mixed lymphocytes during culture (an experimental model mimicking enhancing immunity in human body).

(1) Preparation of human peripheral blood mononuclear cells (PBMCs): following the method in Example 5 (2), peripheral blood PBMCs from two normal human were prepared.

(2) Mixed lymphocyte culture (MLC) reaction with stimulation of pharmaceuticals:

Cell concentrations of freshly isolated peripheral blood mononuclear cells (PBMCs) were adjusted to $5 \times 10^5$/ml with RPMI1640 complete medium. Then, lymphocytes from two healthy human with equal volumes were mixed to maintain a total cell concentration of $1 \times 10^6$/ml. Different concentrations (in a gradient) of or no icariside I were added thereto (with final concentration of 100 ng/ml, 1000 ng/ml) followed by fully mixing. Then the cells after stimulation were seeded and cultured in a 96-well round-bottom culture plate. The cell concentration per well was maintained at $2\times10^5$/ml (200 μl/well) and was incubated at 37° C. with 5% $CO_2$ for 120 h in an incubator. The levels of cytokine IFN-γ were detected.

(3) ELISA Detection for the Levels of Cytokine IFN-γ Production

According to the method stated in Example 5 (4), the γ-interferon generated from human peripheral blood mixed lymphocyte culture (MLC) was detected.

Figure 7:
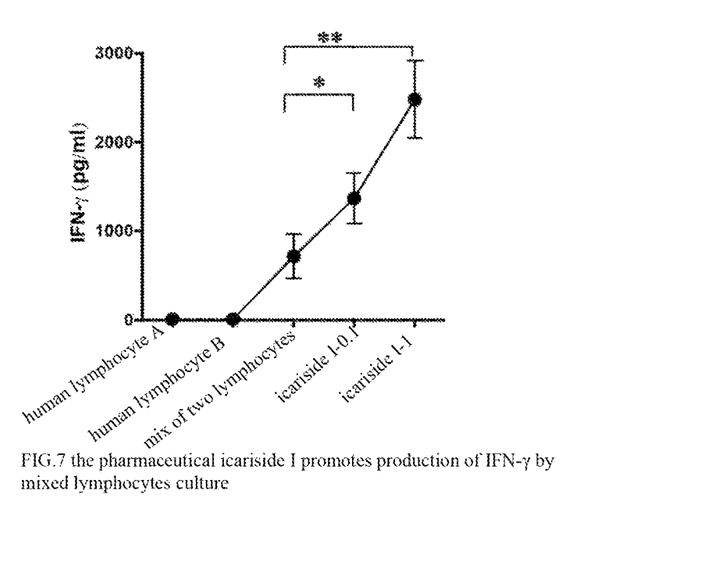
FIG. 7 shows the pharmaceutical icariside I promoting IFN-γ production in a mixed lymphocytes culture in Example 7.

The results were shown in FIG. 7. FIG. 7 showed that after mixed culture of the lymphocytes from two normal human, IFN-γ level was increased. After addition of icariside I, generation of IFN-γ in the mixed lymphocyte culture was significantly promoted in a dose dependent way (up to 300%).

Equal cell concentrations of lymphocytes from healthy human were mixed cultured for five days (120 h). The pharmaceutical icariside I was added (in a gradient of different pharmaceutical concentrations) or not added. Experimental results showed that the pharmaceutical icariside I can significantly promote the production of cytokine IFN-γ. Among them, the human lymphocyte A control is a group of samples containing only one kind of human lymphocyte, while human lymphocyte B control is a group of samples containing two kinds of human lymphocytes, that is, a control group in which two kinds of human lymphocytes were mixed for culture without adding icariside I. The concentrations of icariside I added were 0.1 and 1 μg/ml respectively. *$P<0.05$; **$P<0.01$.

Example 8

Screening Test of the Ability of Icariside Compounds in Promoting Human γ-Interferon Production According to the test stated in Example 7, i.e. using mixed lymphocyte culture (MLC) reaction with stimulation of pharmaceuticals as a screening model, different icariside compounds were subjected to screening to evaluate the ability thereof in promoting human γ-interferon production.

Cell concentrations of freshly isolated peripheral blood mononuclear cells (PBMCs) were adjusted to $5\times10^5$/ml with RPMI1640 complete medium. Then, equal volumes of lymphocytes from two healthy people were mixed for culture and the total cell concentration was maintained at $1\times10^6$/ml. Different icariside I compounds (final concentration at 1000 ng/ml) were added and well-mixed. After stimulation with the pharmaceuticals, the cells were seeded and cultured in a 96-well round-bottom culture plate. The cell concentration per well was maintained at $2\times10^5$/ml (200 μl/well) and the cells were cultured at 37° C. with 5% $CO_2$ for 120 h in an incubator. The level of cytokine IFN-γ produced was then detected.

Figure 8:
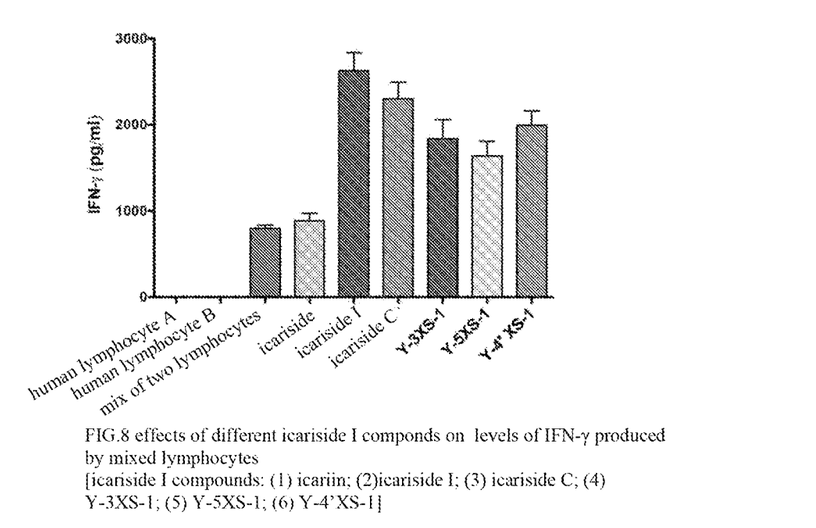
FIG. 8 shows the effect of different icariside I compounds on levels of IFN-γ produced by mixed lymphocytes [icariside I compounds: (1) icariin; (2) icariside I; (3) icariside C; (4) Y-3XS-1; (5) Y-5XS-1; (6) Y-4' XS-1] in Example 8.

The results were shown in FIG. 8. FIG. 8 showed that IFN-γ was increased after culture of mixed lymphocytes from two normal people. After the addition of different icariside I compounds (with final concentration 1000 ng/ml), the IFN-γ production levels in mixed lymphocyte culture were found to have a relatively large difference. This illustrated that different compounds showed different effect on cell immunity.

These test results showed that icariside I had the best ability to promote human γ-interferon production, while icariin showed almost no effect and other analogs showed different degrees of promotion.

Example 9

Test of Icariside I in Promoting Pleural Effusion Cells of Patients Suffering from Tuberculosis to Produce Human γ-Interferon and Thus Enhancing Human Ability to Resist TB Infection.

(1) Isolation of human peripheral blood mononuclear cells (PBMCs): according to the method stated in Example 5 (2), normal human peripheral blood PBMCs were prepared.

(2) Isolation of Pleural fluid cells (PFMCs, namely cells stimulated by tuberculosis bacteria infection) from patients suffering from tuberculosis: blood samples were taken from volunteers (vein blood of TB patients) and then anticoagulated with heparin and diluted with an equal volume of Hank's solution. The solution was centrifuged once (1800 rpm, 22° C. 8 minutes). After removal of the supernatant, an appropriate amount of ELS (erythrocyte lysate) was added for re-suspension. After 3-5 minutes, an appropriate amount of Hank's solution was added for stop and then the mixture was centrifuged twice (1800 rpm, 22° C. 8 minutes), followed by addition of RPMI1640 complete medium to adjust the PBMC cell concentration to $2\times10^9$ cells/L.

(3) PBMCs and PFMCs cell culture (MLC) with stimulation by a pharmaceutical: Icariside I was used at concentrations of 0.1 μg/ml, 0.5 μg/ml, and 1 μg/ml respectively to stimulate PBMCs and PFMCs under the incubation condition at 37° C. with 5% $CO_2$ for 48 hours.

(4) ELISA assay for analysis of IFN-γ: according to the method stated in Example 5 (4), the levels of γ-interferon produced by PBMCs and PFMCs after culture with pharmaceutical stimulations were measured.

Figure 9:
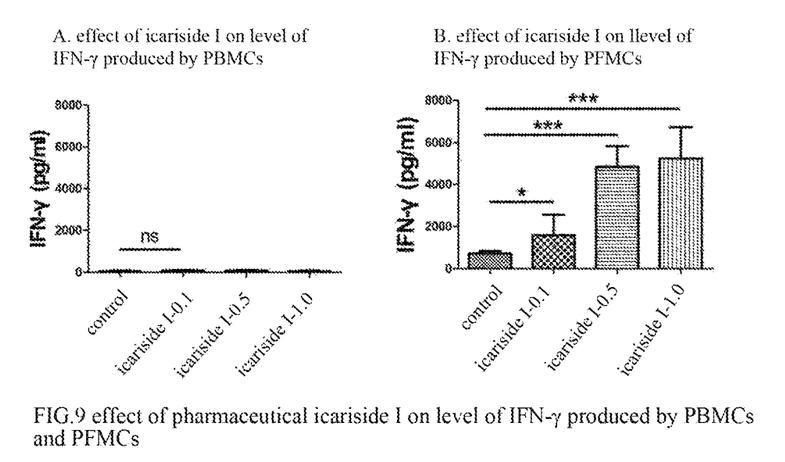
FIG. 9 shows the effect of the pharmaceutical icariside I on level of IFN-γ produced by PBMCs and PFMCs in Example 9.

The results were shown in FIG. 9. FIG. 9 showed that after using icariside I for stimulation in culture, no significant promoting effect was shown for PBMCs in producing IFN-γ, while there was a significant and dose dependent effect for PFMCs in producing IFN-γ. It indicated that icariside I can significantly promote the production of IFN-γ by TB bacteria infected PFMCs (pleural effusion cells of patients suffering from tuberculosis). Results of this test suggest very clearly that, icariside I can improve the body's ability to fight against TB infection and thus it has important promising applications in immunotherapy of tuberculosis.

PBMCs from healthy human and PFMCs from TB infected patients were respectively cultured for 2 days (48 h), then added or not added with the pharmaceutical icariside I (at a gradient of different concentrations). Experimental results showed that icariside I can significantly promote the production level of cytokine IFN-γ in PFMCs of TB infected patients. Among the tests, the concentrations of icariside I added were 0.1, 0.5 and 1 μg/ml. *$P<0.05$; -*$P<0.01$.

Example 10

Test of Icariside I in Inhibiting Tumorigenesis and Tumor Progression in Mice

NIH mice used for the tests were about 18-22 grams and divided into 10 mice per group. The liquid (0.2 ml) of S180 ascites tumor of mice was inoculated subcutaneously into the armpit region of mice. The next day after the inoculation, each group of mice were injected intraperitoneally: (1) physiological saline group; (2) solvent control group (DMSO); (3) positive control group [cyclophosphamide 60 mg/(kg·d)]; (4) low-dose group 1: icariside I 2 mg/(kg·d); (5) low-dose group 2: icariside I 5 mg/(kg·d); (6) middle-dose group: icariside I 10 mg/(kg·d); (7) high-dose group: icariside I 20 mg/(kg·d). After administration for 10 continuous days, the administration was stopped and on the next day, the mice were weighed and sacrificed with tumor mass stripped and weighed. The physiological saline group and solvent group were used as a control for calculation of tumor inhibition rate. The results are shown in Table 1.

TABLE 1

Experimental results of inhibition of tumor growth with icariside I in mice

| Group | number for start | final number | weight of tumor ($\bar{x} \pm SD$, g) | change of body weight (g) | tumor inhibition rate (%) with physiological saline group as control | tumor inhibition rate (%) with solvent group as control |
|---|---|---|---|---|---|---|
| physiological saline group | 10 | 10 | 1.04 ± 0.54 | +16.1 | — | — |
| solvent group (25% DMSO) | 10 | 10 | 1.34 ± 0.60 | +12 | — | — |
| positive control cyclophosphamide group (60 mg/Kg) | 10 | 10 | 0.6 ± 0.06 | +4.5 | 42.3 | 55.2 |
| icariside I low dose group (2 mg/Kg) | 10 | 10 | 0.98 ± 0.47 | +11.6 | 5.8 | 26.9 |
| icariside I low dose group (5 mg/Kg) | 11 | 11 | 0.77 ± 0.47 | +12.5 | 26.0 | 42.5 |
| icariside I middle dose group (10 mg/Kg) | 10 | 10 | 0.64 ± 0.25 | +10.6 | 38.5 | 52.2 |
| icariside I high dose group (20 mg/Kg) | 10 | 10 | 0.34 ± 0.12 | +9.0 | 67.3 | 74.6 |

The results in Table 1 show that icariside I can significantly inhibit tumorigenesis and tumor progression in mice with an effect better than that of the positive control pharmaceutical cyclophosphamide.

Example 11

Test of Effect of Icariside I on Xenograft Tumor Growth in Nude Mice

Figure 10:
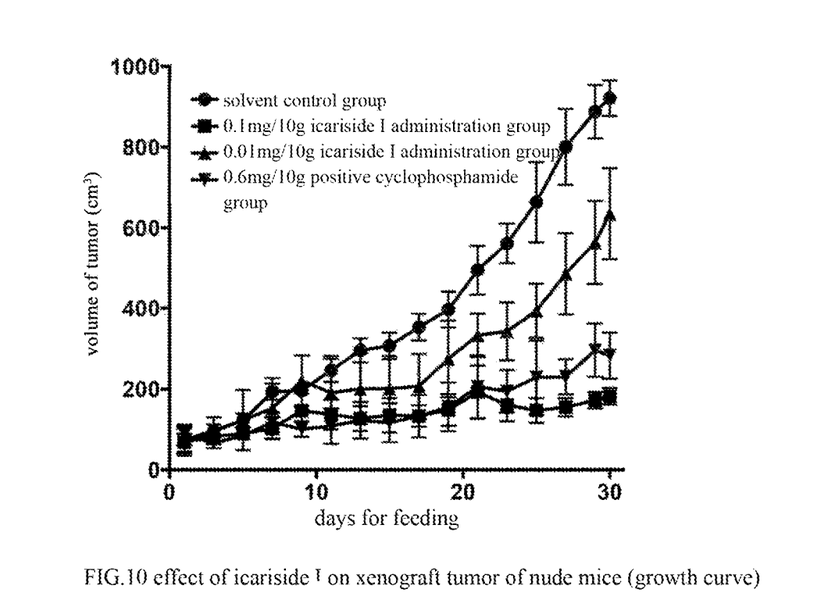
FIG. 10 shows the effect of icariside I on xenograft tumor in nude mice (growth curve) in Example 11.
Figure 11:
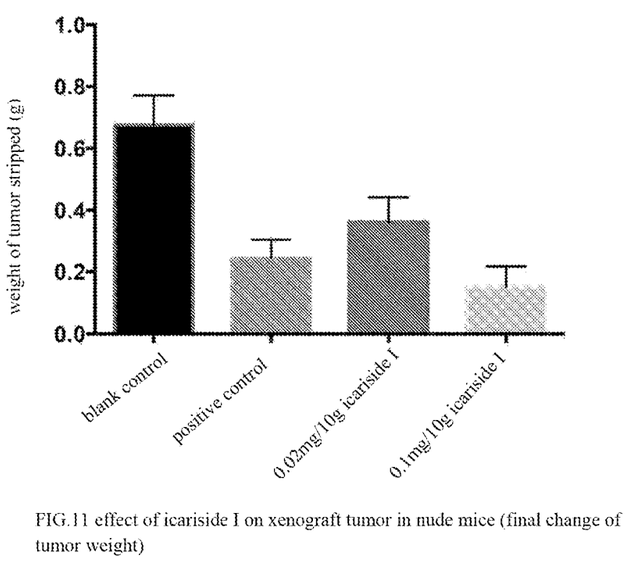
FIG. 11 shows the effect of icariside I on xenograft tumor in nude mice (final change of tumor weight) in Example 11

The test used 4-6 weeks old BALB/c (nu/nu) female nude mice weighed 18-22 g fed in a SPF clean room with free access to food and water. Models were established with 40 nude mice by transplanting tumor mass. When the tumor grew to the initial volume for administration with a pharmaceutical (100 mm³), these mice were divided into groups with 10 mice for each group. For each group, nude mice were injected intraperitoneally: (1) the blank control group was injected with 0.1 ml/10 g solvent (5% DMSO+95% physiological saline); (2) the positive pharmaceutical injection group [cyclophosphamide (0.6 mg/10 g)]; (3) administration group (icariside I): high concentration group injected with: 0.1 mg/10 g; low concentration group injected with: 0.02 mg/10 g. The administration was conducted every 2 days in a 30-day period. Vernier caliper was used to measure the largest longitudinal diameter (L) and transverse diameter (S) of tumor every two days. The approximate volume of the tumor was calculated with the equation of V (cm³)=0.5×L× S² to plot a tumor growth curve. After the pharmaceutical treatment, the tumor was stripped and weighed for record. The results were shown in FIGS. 10 and 11. It is shown that icariside I can significantly inhibit growth and development of the transplanted tumor mass in nude mice with an effect better than that of the positive control pharmaceutical cyclophosphamide.

Example 12

Acute Toxicity Test for Icariside I

Mice weighed 18-22 grams were randomly divided into six groups with 10 mice each group. Each individual group of mice were treated (orally) with: physiological saline, DMSO 2.5 ml/kg, and icariside I: 2000 mg/kg, 1000 mg/kg, 500 mg/kg, 100 mg/kg respectively. After observation for 14 days, none of the test mice died. The results show that the acute toxicity LD50 value of icariside I in mice is greater than 2000 mg/kg. Therefore, the acute toxicity of icariside I is very low which is safe for use in preparation of pharmaceuticals, health products, food, and cosmetic and skin care products for prevention and treatment of immunity-related diseases.

The disclosure claimed is:

1. A method for treating ascites cancer or tuberculosis comprising administering to a subject in need thereof a therapeutically effective amount of icariside compounds having the following formula:

wherein:

$R_1$ is OH, $R_2$ is OH, and $R_3$ is OCH3:

wherein the icariside compounds improve subject immunity by promoting subject cells to produce γ-interference.

2. A method for treating ascites cancer or tuberculosis comprising administering to a subject in need thereof a therapeutically effective amount of icariside compounds having the following formula:

wherein:
R$_1$ is OH, R$_2$ is OH, R$_3$ is OH;
wherein the icariside compounds improve subject immunity by promoting subject cells to produce γ-interference.

3. A method for treating ascites cancer or tuberculosis comprising administering to a subject in need thereof a therapeutically effective amount of icariside compounds having the following formula:

wherein:
R$_1$ is OCH$_3$, R$_2$ is OH, R$_3$ is OCH$_3$; or;
R$_1$ is OH, R$_2$ is OCH$_3$, R$_3$ is OCH$_3$;
wherein the icariside compounds improve subject immunity by promoting subject cells to produce γ-interference.

* * * * *